(12) United States Patent
Gjesdal et al.

(10) Patent No.: US 11,138,729 B2
(45) Date of Patent: Oct. 5, 2021

(54) PROCESSING MRI DATA FOR ANALYSIS OF TUMORS

(71) Applicants: OSLO UNIVERSITETSSYKEHUS HF, Oslo (NO); AKERSHUS UNIVERSITETSSYKEHUS HF, Lørenskog (NO)

(72) Inventors: Kjell-Inge Gjesdal, Ålesund (NO); Endre Grøvik, Oslo (NO); Kathrine Røe Redalen, Fjerdingby (NO); Tryggve Holck Storås, Oslo (NO)

(73) Assignees: OSLO UNIVERSITETSSYKEHUS HF, Oslo (NO); AKERSHUS UNIVERSITETSSYKEHUS HF, Lorenskog (NO)

( * ) Notice: Subject to any disclaimer, the term of this patent is extended or adjusted under 35 U.S.C. 154(b) by 429 days.

(21) Appl. No.: 16/092,036

(22) PCT Filed: Apr. 20, 2017

(86) PCT No.: PCT/EP2017/059368
§ 371 (c)(1),
(2) Date: Oct. 8, 2018

(87) PCT Pub. No.: WO2017/182557
PCT Pub. Date: Oct. 26, 2017

(65) Prior Publication Data
US 2019/0156479 A1 May 23, 2019

(30) Foreign Application Priority Data
Apr. 21, 2016 (GB) ..................... 1606916

(51) Int. Cl.
*G06T 7/00* (2017.01)
*A61B 5/055* (2006.01)
*A61B 5/00* (2006.01)

(52) U.S. Cl.
CPC ............ *G06T 7/0014* (2013.01); *A61B 5/055* (2013.01); *A61B 5/418* (2013.01); *A61B 5/7275* (2013.01);
(Continued)

(58) Field of Classification Search
CPC ....... A61B 5/055; A61B 5/418; A61B 5/7275; A61B 5/7485; A61B 2576/02;
(Continued)

(56) References Cited

U.S. PATENT DOCUMENTS

| | | |
|---|---|---|
| 3,789,832 A | 2/1974 | Damadian |
| 2014/0107469 A1 | 4/2014 | Gjesdal et al. |
| 2014/0271470 A1 | 9/2014 | Sillerud et al. |

FOREIGN PATENT DOCUMENTS

| | | |
|---|---|---|
| WO | 2008147921 A1 | 12/2008 |
| WO | 2012070951 A1 | 5/2012 |

OTHER PUBLICATIONS

Yao et al., "Rectal cancer: 3D dynamic contrast-enhanced MRI; correlation with mircovascular density and clinicopathological features" Radiol med (2011) 116:366-374 (Year: 2011).*

(Continued)

*Primary Examiner* — Boniface N Nganga
(74) *Attorney, Agent, or Firm* — Eversheds Sutherland (US) LLP (57) ABSTRACT

Dynamic contrast enhanced MRI data and dynamic susceptibility contrast MRI data for a volume of the patient's body including a tumor are used in order to identify the risk of lymph node metastasis. A volume of interest enclosing the tumor is identified and the MRI data for the volume of interest is processed in order to identify one or more parameters relating to the transverse relaxation rate and/or to dynamic changes in the transverse relaxation rate. A comparison is made to previously obtained similar parameters (Continued)

for other patients having similar tumors that are either known to exhibit lymph node metastasis or are known not to exhibit lymph node metastasis in order to determine if the MRI data indicates that the patient has a tumor at greater risk of exhibiting lymph node metastasis or a tumor with a lesser risk of exhibiting lymph node metastasis.

14 Claims, 6 Drawing Sheets (52) U.S. Cl.
CPC ........ *A61B 5/7485* (2013.01); *A61B 2576/02* (2013.01); *G06T 2207/10088* (2013.01); *G06T 2207/30096* (2013.01)

(58) Field of Classification Search
CPC ......... G06T 7/0014; G06T 2207/10088; G06T 2207/30096
See application file for complete search history.

(56) References Cited

OTHER PUBLICATIONS

International Search Report and Written Opinion, PCT/EP2017/059368, dated Jun. 28, 2017 (17 pages).

Search Report, GB1606916.3, dated Nov. 21, 2016 (6 pp.).

Alberda, W.J., et al., Predition of tumor stage and lymph node involvement with dynamic contrast-enhanced MRI after chemoradiotherapy for locally advanced rectal cancer, Springer-Verlag 2012, Int J Colorectal Dis (2013) 28:573-580, DOI 10.1007/s00384-012-1576-6 (8 pp.).

Chuanming, L., et al., The Value of T2* in Differentiating Metastatic from Benign Axillary Lymph Nodes in Patients with Breast Cancer—A Preliminary in Vivo Study, Open Access, PLOSlone, vol. 9, Issue 1, e84038, Jan. 2014 (5 pp.).

Grøvik, E., et al., DSC MR-mammography: Tumor characterization using quantitative R2* analysis, Proc. Intl. Soc. Mag. Reson. Med. 18 (2010) (1 p.).

Grøvik, E., et al., Single Bolus Split Dynamic MRI: Is the Combination of High Spatial and Dual-Echo High Temporal Resolution Interleaved Sequences Useful in the Differential Diagnosis of Breast Masses?,Journal of Magnetic Resonance Imaging 42:180-187 (2015) (8 pp.).

Koh, M.J., et al., Which is the best advanced MR imaging protocol for predicting recurrent metastatic brain tumor following gamma-knife radiosurgery: focused on perfusion method, Springer, Neuroradiology (2015) 57:367-376,DOI 10.1007/s00234-015-1485-9 (10 pp.).

Korteweg, M.S., et al., Gadofosveset as a negative contrast agent for detecting metastatic axillary lymph nodes in breast cancer patients on diffusion, Proc. Intl. Soc. Mag. Reson. Med. 18 (2010) (1 p.).

* cited by examiner

PROCESSING MRI DATA FOR ANALYSIS OF TUMORS

TECHNICAL FIELD

The present invention relates to a method for processing MRI data for analysis of tumors as well as to a related data processing apparatus and computer programme product. The method may be for identifying characteristics of the tumor and in particular may be for identifying patients with tumors having a greater risk of metastasis.

BACKGROUND OF THE INVENTION

As is well known, cancers affect numerous patients across the world and can often lead to severe health complications and death. There is an ongoing need to improve techniques for the identification, assessment, and treatment of cancerous conditions. Magnetic Resonance Imaging (MRI) has become an important tool for the analysis of cancerous tumors both through the ability for medical professionals to view detailed images of the patient's body, and also through the use of automated analysis of MRI data in order to provide information concerning the patient's condition.

For example, US 2014/107469 describes a technique making use of dynamic contrast enhanced MRI as a diagnostic tool for examining breast cancer tissue, including methods for processing the data in order to find parameters that are considered to be indicative of whether or not the breast cancer is benign or malignant. The techniques described in the document represented an important advance in this field, but further work is still required and improvements are still possible.

SUMMARY OF THE INVENTION

Viewed from a first aspect, the present invention provides a method for processing MRI data for analysis of tumors, the method comprising: obtaining dynamic contrast enhanced MRI data and dynamic susceptibility contrast MRI data for a volume of the patient's body including a tumor; identifying a volume of interest enclosing the tumor; processing the MRI data for the volume of interest in order to identify one or more parameters relating to the transverse relaxation rate and/or to dynamic changes in the transverse relaxation rate; comparing the one or more parameters to previously obtained similar parameters for multiple other patients having similar tumors that are either known to exhibit lymph node metastasis or are known not to exhibit lymph node metastasis; and thereby determining if the MRI data indicates that the tumor is at a greater risk of exhibiting lymph node metastasis or at a lesser risk of exhibiting lymph node metastasis.

As described in further detail below the inventors have found that parameters relating to the transverse relaxation rate and to dynamic changes in the transverse relaxation rate differ between a patient with a tumor at greater risk of exhibiting lymph node metastasis and a patient with a tumor having a lesser risk of exhibiting lymph node metastasis. The method of the first aspect consequently provides a significant advance by allowing for effective assessment of the risk of lymph node metastasis based on MRI data. In the prior art, including US 2014/107469 mentioned above, there is no consideration of distinguishing between different patients with malignant tumors based on propensity for metastising. The proposed method does not result in a diagnosis by itself but can be used as a part of a method for diagnosis for cancer patients and can aid a more precise diagnosis. A full diagnosis in this context requires histopathology (tumor biopsy), the T stage (from MRI), the N stage (from MRI) and M stage (from MRI or CT) and consultation with at least one of each of gastrosurgeons, pathologists, oncologists and radiologists. The proposed method can provide a means for finding patients that are positive N stage, but this by itself does not lead to a medical diagnosis. Identifying tumors at greater risk of lymph node metastasis will also allow for more accurate identification of patients that would benefit from intensified treatments and/or can improve the selection of patients that are in need of preoperative treatments such as chemo radiotherapy.

In particular, it has been found that lower values for transverse relaxation rate or dynamic changes in transverse relaxation rate indicate a higher potential for lymph node metastasis, and thus the method may include determining if the MRI data indicates a patient with a tumor at greater risk of exhibiting lymph node metastasis by comparison of the one or more parameters with the previously obtained similar parameters and determining if the one or more parameters are similar to previously obtained similar parameters for patients having similar tumors that are known to exhibit lymph node metastasis and/or determining if the one or more parameters are lower than previously obtained similar parameters for patients having similar tumors that are known not to exhibit lymph node metastasis. The method may include the use of a threshold value determined based on the previously obtained similar parameters, and optionally the method may include determining such a threshold. The threshold value may, for example, be set as a value lying between the previously obtained similar parameters for patients having similar tumors that are known to exhibit lymph node metastasis and the previously obtained similar parameters for patients having similar tumors that are known not to exhibit lymph node metastasis.

The one or more parameters relating to the transverse relaxation rate and/or to dynamic changes in the transverse relaxation rate may include one or more of: the peak change in tumor $R_2^*$, the dynamic peak change in tumor $R_2^*$, a maximum of the peak change or the dynamic peak change, and/or an integral for dynamic peak change in tumor $R_2^*$ over a time period, such as a time period centred on a maximum value. The tumor $R_2^*$ may be tumor $R_2^*$ during bolus first pass, and in particular may be wash-in $R_2^*$ peak enhancement.

It is preferred for both of the dynamic contrast enhanced MRI data and the dynamic susceptibility contrast MRI to be obtained in a single dynamic examination.

Metastasis as referenced herein is typically lymph node metastasis and it will be noted that the discussion above is restricted to lymph node metastasis. However, it is also envisaged that the same technique may be applied to other types of metastasis, such as distant metastasis of different organs (e.g. metastasis from a rectal tumor to the lungs or liver). Consequently, it should be understood that in a broader aspect, although not currently claimed, the invention extends to the method of the first aspect as well as to the apparatus of the second aspect and the computer programme product of the third aspect with any type of metstasis being the focus, wherein the previously obtained similar parameters are in relation to patients with known status in relation to the metastasis of interest.

The tumor can be any tumor type. In some examples, as described below, the tumor is a rectal tumor. The method may hence be a method for processing MRI data concerning rectal tumors in order to determine if the patient is at a greater or lesser risk of lymph node metastasis.

The step of identifying a volume of interest may include automated identification of a volume of interest via computer software, such as via image analysis. This could be a fully or semi-automated process. One possibility involves the operator identifying a location within the tumor, with image analysis algorithms then identifying the borders of the tumor volume of interest by expanding outwards from this location. The volume of interest identified in this way may be checked by medical personnel before it is used further in later parts of the method. It is currently preferred to have some human input to ensure accurate definition of the volume of interest. Thus, alternatively or additionally there may be identification of a volume of interest by one or more medical personnel, for example based on MRI images. This may be done by manually tracing on the image to identify the volume of interest. The method may include the use of two independently identified volumes of interest, identified by different medical personnel, in order to minimise the risk of an error in identification of the volume of interest that may result in an incorrect analysis of the data. The volume of interest may be determined based on $T_2$ weighted and/or diffusion weighted images.

A particular example is described below and the method may include the use of calculations as described in this example.

Viewed from a second aspect, the present invention provides a data processing apparatus for processing MRI data for analysis of tumors, the data processing apparatus comprising: an MRI data receiving module for receiving dynamic contrast enhanced MRI data and dynamic susceptibility contrast MRI data for a volume of the patient's body including a tumor; a volume of interest identification module for generating and/or receiving data identifying a volume of interest enclosing the tumor; and an MRI data processing module for processing the MRI data for the volume of interest and being arranged to: identify one or more parameters relating to the transverse relaxation rate and/or to dynamic changes in the transverse relaxation rate, compare the one or more parameters to previously obtained similar parameters for multiple other patients having similar tumors that are either known to exhibit lymph node metastasis or are known not to exhibit lymph node metastasis, and thereby determine if the MRI data indicates that the tumor is at a greater risk of exhibiting lymph node metastasis or at a lesser risk of exhibiting lymph node metastasis.

This apparatus provides the same advantages as the method of the first aspect. By use of the apparatus it is possible to improve the diagnosis and treatment of patients. The apparatus may be used for processing MRI data concerning rectal tumors.

The MRI data receiving module, the volume of interest identification module and/or the MRI data processing module may be hardware of software modules of the data processing apparatus. In each case the module(s) may be a single hardware or software element, or they may be made of a grouping of hardware or software elements. The MRI data receiving module, the tumor identification module and/or the MRI data processing module may share common hardware and/or common software. In one example the data processing apparatus is a computer device arranged to receive MRI data from an MRI imaging apparatus, with a computer processor arranged to allow for automated or user-defined identification of the volume of interest. The computer device may be separate to the MRI imaging apparatus or it may be joined or integrated therewith, for example as a part of an MRI imaging system.

There may be data storage for storing the previously obtained similar parameters, with the data processing module being arranged to access the stored previously obtained similar parameters in the comparing step.

The data processing module may be arranged to determine if the MRI data indicates a patient with a tumor at greater risk of exhibiting lymph node metastasis by comparison of the one or more parameters with the previously obtained similar parameters and determining if the one or more parameters are similar to previously obtained similar parameters for patients having similar tumors that are known to exhibit lymph node metastasis and/or determining if the one or more parameters are lower than previously obtained similar parameters for patients having similar tumors that are known not to exhibit lymph node metastasis. A threshold value determined based on the previously obtained similar parameters may be used, and this may be stored at the data processing apparatus, for example in the data storage thereof. Optionally the data processing module may be arranged to determine such a threshold. The threshold value may, for example, be set as a value lying between the previously obtained similar parameters for patients having similar tumors that are known to exhibit lymph node metastasis and the previously obtained similar parameters for patients having similar tumors that are known not to exhibit lymph node metastasis.

The one or more parameters relating to the transverse relaxation rate and/or to dynamic changes in the transverse relaxation rate may include one or more of: the peak change in tumor $R_2^*$, the dynamic peak change in tumor $R_2^*$, a maximum of the peak change or the dynamic peak change, and/or an integral for dynamic peak change in tumor $R_2^*$ over a time period, such as a time period centred on a maximum value. The tumor $R_2^*$ may be tumor $R_2^*$ during bolus first pass, and in particular may be wash-in $R_2^*$ peak enhancement.

The data processing apparatus may further comprise an MRI control module for controlling an MRI apparatus to obtain the required MRI data, which is then received by the MRI data receiving module. The MRI control module may be arranged to control the MRI apparatus in order to obtain both of the dynamic contrast enhanced MRI data and the dynamic susceptibility contrast MRI in a single dynamic examination.

The volume of interest identification module may be arranged for automated identification of a volume of interest via computer software, such as via image analysis. This could be a fully or semi-automated process. One possibility involves the volume of interest identification module being arranged to receive an indication of a location within the tumor from the operator, with the volume of interest identification module including image analysis algorithms for identifying the borders of the tumor volume of interest by expanding outwards from this location.

Alternatively or additionally, the volume of interest identification module may be arranged to receive data for identification of a volume of interest input by one or more medical personnel, for example based on MRI images. This may be done by manually tracing on the image to identify the volume of interest. The data processing apparatus may hence include or be connectable to a user interface for interaction with medical personnel in order to allow input that identifies the volume of interest. The data processing module may be arranged to compare data for two independently identified volumes of interest in order to minimise the risk of an error in identification of the volume of interest that may result in an incorrect analysis of the data. The volume of interest may be determined based on $T_2$ weighted and/or diffusion weighted images and the data processing apparatus may be arranged to provide such images via the user interface for user input and/or to the volume of interest identification module for image analysis.

The invention further extends to a computer programme product containing instructions that, when executed, will configure a data processing apparatus to perform the method of the first aspect and, in some examples, the optional features thereof, or to operate in accordance with the data processing apparatus of the second aspect and, in some examples, the optional features thereof.

Viewed from a third aspect, the present invention provides a computer programme product containing instructions that, when executed, will configure a data processing apparatus to: receive dynamic contrast enhanced MRI data and dynamic susceptibility contrast MRI data for a volume of the patient's body including a tumor; receive data identifying a volume of interest enclosing the tumor; process the MRI data for the volume of interest in order to identify one or more parameters relating to the transverse relaxation rate and/or to dynamic changes in the transverse relaxation rate; compare the one or more parameters to previously obtained similar parameters for multiple other patients having similar tumors that are either known to exhibit lymph node metastasis or are known not to exhibit lymph node metastasis; and thereby determine if the MRI data indicates that the tumor is at a greater risk of exhibiting lymph node metastasis or at a lesser risk of exhibiting lymph node metastasis.

The data processing apparatus may be an apparatus for processing MRI data for analysis of tumors as described in the second aspect and the computer programme product may hence be arranged to configure modules to act as in the second aspect. The computer programme product may contain instructions that, when executed, will configure the data processing apparatus to perform any of the functions described above in connection with the first or second aspect. The computer programme product may include image analysis algorithms for identifying the borders of the tumor volume of interest by expanding outwards from a location indicated by an operator of the apparatus.

This includes optionally the use of calculations as described in the example embodiment set forth in detail below.

BRIEF DESCRIPTION OF THE DRAWINGS

Certain preferred embodiments will now be described by way of example only and with reference to the accompanying drawings in which.

DETAILED DESCRIPTION OF THE INVENTION

Introduction

Current international guidelines recommend magnetic resonance imaging (MRI) as part of primary staging of rectal cancer. MRI helps identify patients with increased risk of local recurrence and the need of neoadjuvant chemoradiotherapy. Despite improvements in multimodal rectal cancer management during the past decades, with local recurrence rates below 10%, a considerable number of patients experience poor disease outcome resulting from metastatic disease progression. Reliable detection of metastatic lymph nodes (N+ stage), a main prognostic indicator of distant metastasis, is still a challenge in rectal cancer MRI. At present, the most accurate criterion is the morphological finding of irregular-contoured nodes with heterogeneous signal pattern. However, these MRI findings are associated with substantial misinterpretation and the diagnostic accuracy is relatively poor. A recent meta-analysis of 21 clinical studies showed an accuracy for lymph node staging of 71%.

To improve the ability of MRI to predict patients at risk of developing metastatic disease, considerable interest is focusing on the tumor microenvironment. Dynamic contrast-based MRI is an increasingly popular method for tumor characterization, enabling quantitative assessment of phenotypic properties. The most commonly used dynamic acquisition is dynamic contrast-enhanced (DCE) MRI, enabling assessment of tissue properties such as capillary permeability and extracellular volume fraction. There is currently no consensus concerning the role of DCE-MRI in rectal cancer patients.

Dynamic susceptibility contrast (DSC) MRI is most commonly used to measure perfusion in the brain. However, several studies have also shown the feasibility of using this approach to assess phenotypic characteristics of breast tumors. To our knowledge, DSC-MRI analysis has never before been applied in rectal cancer. Recognizing that rectal tumors are highly angiogenic, it is hypothesized that DSC-MRI may provide valuable information for assessing pathophysiological properties in this patient group.

Multiple echoes can be acquired in a high temporal resolution dynamic contrast-based MRI sequence, allowing quantitative measurements of the dynamic change in both longitudinal- ($R_1=1/T_1$) and transverse relaxation rate ($R_2^*=1/T_2^*$). As a result, DCE- and DSC-data can be obtained during a single dynamic examination, thus yielding information on pathophysiological properties related to both tissue-permeability and perfusion. In earlier studies, the feasibility of a multi-echo MRI technique was demonstrated through both simulations and in the assessment of breast cancer.

The aim of this study was to implement a dynamic contrast-based multi-echo MRI sequence in the assessment of rectal cancer, and to evaluate associations between clinicopathological data and the attainable DCE- and DSC-MRI parameters.

Materials and Methods
Study Patients

The investigation was performed within the prospective biomarker study OxyTarget—Functional MRI of Hypoxia-Mediated Rectal Cancer Aggressiveness (NCT01816607), approved by the Institutional Review Board and the Regional Committee for Medical and Health Research Ethics of South East Norway. The study was performed in accordance with the Helsinki declaration and written informed consent for participation.

The principal inclusion criterion was histologically confirmed rectal cancer scheduled to radical treatment. The patient cohort within the present study was enrolled between March 2014 and June 2015 and all cases had primary pelvic surgery. The resected tumor specimens underwent standard histopathologic staging (pTN), including determination of the absence or presence of extramural venous invasion. Patient and tumor characteristics are provided in Table 1 below.

TABLE 1

Patient and tumor characteristics

| | |
|---|---|
| No. of patients | 17 |
| Gender | |
| Male | 11 (64.7%) |
| Female | 6 (35.3%) |
| Median age (years)[a] | 66 (50-88) |
| Male | 66 (52-88) |
| Female | 71 (50-77) |
| Median tumor volume (cm³)[a,b] | 18.8 (4.5-64.0) |
| rTNM stages[c] | |
| mrT1 | 2 (11.8%) |
| mrT2 | 5 (29.4%) |
| mrT3 | 8 (47.1%) |
| mrT4 | 2 (11.8%) |
| mrN0 | 10 (58.8%) |
| mrN1 | 6 (35.3%) |
| mrN2 | 1 (5.9%) |
| rM0 | 16 (94.1%) |
| rM1 | 1 (5.9%) |
| Surgery | |
| Low anterior resection | 13 (76.5%) |
| Abdominal perineal resection | 3 (17.6%) |
| Transanal endoscopic microsurgery | 1 (5.9%) |
| pTN stages[d] | |
| pT1 | 4 (23.5%) |
| pT2 | 4 (23.5%) |
| pT3 | 8 (47.1%) |
| pT4 | 1 (5.9%) |
| pN0 | 10 (58.8%) |
| pN1 | 6 (35.3%) |
| pN2 | 1 (5.9%) |
| Extramural venous invasion[d] | |
| Yes | 6 (35.3%) |
| No | 11 (64.7%) |

NOTE.
Except where indicated, data are numbers of patients, with percentages in parentheses
[a]Numbers in parentheses are age ranges
[b]Mean tumor volumes calculated from two independent radiologists' tumor delineations in magnetic resonance images (MRI)
[c]Assessed with MRI or computed tomography (CT) according to the tumor-node-metastasis system. Prefix 'mr' denotes MRI-assessed staging, prefix 'r' denotes radiologically assessed staging (MR and/or CT)

MRI Acquisition

In this pilot study, 24 patients were examined, of which five were excluded because of bowel motion and two because of image artifacts. Imaging was performed on a Philips Achieva 1.5T system (Philips Healthcare, Best, The Netherlands) with NOVA Dual HP gradients (33 mT/m maximum gradient amplitude, 180 T/m/s slew rate). A five channel cardiac coil with parallel imaging capabilities was applied. Glucagon (1 mg/ml, 1 ml intramuscularly) and buscopan (20 mg/ml, 1 ml intravenously) were given to reduce bowel peristalsis. Conventional high-resolution fast spin-echo $T_2$-weighted images of the pelvic cavity and rectum were obtained in the sagittal and transversal planes as well as perpendicular to the tumor axis (TR=2820-3040 ms, TE=80 ms, acquisition matrix=256×230, slice thickness=2.5 mm, number of excitations=6 and echo train length=20).

Dynamic contrast-based multi-echo data were acquired by a 3D $T_1$-weighted multi-shot EPI sequence with three echoes. TR=39 ms, TE1=4.6 ms, echo spacing=9.3 ms, flip angle=28°, EPI factor=9. The acquired matrix size was 92×90 over a 180×180 mm field-of-view (FOV). Twelve slices were acquired with a thickness of 10 mm. The temporal resolution was approximately 2 s/imaging volume with 60 dynamic series acquired. A ProSet fat suppression technique was applied along with a parallel imaging (SENSE) factor of 1.7 in the RL direction. All slices were acquired parallel to the $T_2$-weighted images perpendicular to the tumor axis.

The dynamic multi-echo sequence was interleaved with a high spatial resolution 3D $T_1$-weighted TFE sequence (THRIVE), as part of a split-dynamic MRI framework detailed in a recent study (13). In this framework, one set of THRIVE baseline images was initially acquired. The dynamic multi-echo sequence was then started and 5-7 baseline acquisitions were obtained prior to CA administration. The multi-echo acquisition was repeated approximately 30 times during the wash-in phase, immediately followed by the first post-contrast THRIVE acquisition. During the intermediate and late post-contrast phase, 6 split sessions were conducted, acquiring 4 multi-echo data sets and interleaved THRIVE images. In addition, a series of 14 multi-echo data sets were acquired after the last THRIVE segment to improve curve fitting for kinetic modeling. To avoid non-steady state effects, a 2500 ms dummy repetition (i.e., no data sampling) was run in the beginning of each multi-echo segments. Only results from the dynamic multi-echo data are reported in this work.

A dose of 0.2 mL/kg body weight of gadolinium-based CA (Dotarem® 279.3 mg/mL, Guerbet, Roissy, France) was injected as a bolus (3 mL/s) directly followed by 20 ml of physiologic saline solution.

Simulations

Given that the multi-echo acquisition was run as part of a split-dynamic MRI framework, simulations were performed to investigate whether the splitting of dynamic time-series influences the reliability of parameter estimation in comparison with a continuous acquisition. The simulations were a series of Monte Carlo simulations to investigate whether a split dynamic acquisition technique influences the reliability of parameter estimation in dynamic MR-measurements in comparison with a conventional continuous acquisition. The simulations were performed using in-house algorithm developed in MATLAB (The MathWork Inc. version 7.14.0.739 (R2012a), Natick, Mass., USA).

A system input function was simulated as a gamma variate function with an additional exponential term in order to simulate steady state effects. Corresponding tissue CA-concentration time curves were simulated according to the extended Tofts model (7) by randomly selecting the kinetic parameters within a defined range of values; 0.13-3.17 min$^{-1}$ for $K^{trans}$, 0-80% for $v_e$ and 0-20% for $v_p$. The selected $K^{trans}$- and $v_e$-range were based on values previously observed in a clinical rectal cancer study, and was defined as the mean value±two standard deviations (SD). The bolus-arrival-time (BAT) was randomly selected between 0-10 seconds, and a random Gaussian noise corresponding to a signal-to-noise ratio (SNR) of 20 at a temporal resolution of 2 seconds was added to the CA-concentration time curves. The selected SNR was based on values observed in the patient data.

To investigate the reliability of the split dynamic acquisition technique in comparison with a conventional continuous acquisition, one thousand simulations were performed with a fixed temporal resolution of 2 seconds. The system input function and tissue response curves were then resampled using the split dynamic scheme as implemented in the split dynamic technique, before adding noise based on the selected SNR. Kinetic parameter estimates for the continuous- and splitted CA concentration time curves were then obtained.

The goodness of fit for a given parameter estimation was evaluated by plotting the nominal parameter value against the estimated value and performing linear regression analysis, including model residuals and residual norms to the resulting plots. Mann-Whitney U test was used to test the difference between the split dynamic acquisition and the continuous acquisition, with the null hypothesis that the data obtained from the two acquisition methods are samples from continuous distributions with equal medians. A statistical significance level of 5% was used.

Image Analysis

Diagnostic radiological TNM stages were assessed according to international guidelines and the $7^{th}$ edition TNM staging system. Guided by $T_2$-weighted and diffusion-weighted images, two radiologists with 14 and 7 years of experience (Reader 1 and Reader 2) independently contoured whole-tumor volume-of-interests (VOI) by means of free-hand delineations.

Image post-processing was performed using the nordicICE software (NordicNeuroLab, Bergen, Norway). CA concentration-time curves were estimated from the first echo using the spoiled gradient echo (SPGR) signal equation, denoted $S_{SPGR}(t)$, with the $T_2$ term ignored and assuming a linear relationship between the CA concentration and change in $R_1$ ($1/T_1$):

$$C_t(t) = \frac{(1/T_1(t)) - 1/T_{1,0}}{r_1} \quad 1]$$

where $r_1$ is the longitudinal relaxivity of the CA and $T_{1,0}$ is the $T_1$ of the tissue in the absent of CA. The signal from a SPGR is given by:

$$S_{SPGR}(t) = S_0 \frac{\sin\alpha(1 - e^{-TR/T_1(t)})}{1 - \cos\alpha(e^{-TR/T_1(t)})} \quad 2]$$

where $S_0$ is proportional to the thermal equilibrium magnetization, TR is the repetition time of the sequence, and $\alpha$ is the flip angle. Pre-contrast $T_1$-values were estimated in six patients using a modified Look-Locker inversion recovery (MOLLI) technique. Average $T_1$-values (±standard deviation) were measured to 1528±40 ms in blood and 1354±103 ms in cancer tissue and used as a fixed $T_1$-baseline for SPGR signal conversion in arteries and tumors, respectively. The measured $T_1$-values in blood agreed well with literature values.

The CA concentration-time curves were then analyzed on a voxel-by-voxel basis using the extended Tofts pharmacokinetic model:

$$C_t(t) = K^{trans} C_a(t) \otimes e^{-\frac{K^{trans}}{v_e}t} + v_p C_a(t) \quad 3]$$

where $\otimes$ represents the convolution operator and $K^{trans}$ is the volume transfer constant between the plasma volume, $v_p$, and the extravascular extracellular space volume, $v_e$. An arterial input function (AIF), $C_a$, was obtained for each patient by extracting the CA concentration-time curve from an artery supplying the region of interest (ROI) using an automatic cluster-algorithm, and an average AIF was generated and used for quantitative analysis. The enhancement delay between the AIF- and the VOI-signal were manually measured and included as a fixed variable in the kinetic model. Voxel-wise CA concentration-time curves were also analyzed by estimating the maximum peak enhancement ($\text{Peak}_{enh}$), time-to-peak (TTP), area under the curve (AUC), wash-in and wash-out rate.

From the multi-echo data, voxel-wise dynamic change in $R_2^*$ was estimated by assuming a mono-exponential signal-dependent change as a function of TE:

$$SI(t_m, TE_n) = SI_0(t_m) e^{-TE_n \cdot R_2^*(t_m)} \quad 4]$$

where the subscript m=1, . . . , M labels the repetition of the multi-echo acquisition, n=1, . . . , N labels the echo number, and $SI_0(t_m)$ is the initial signal amplitude. The TE-dependent signal was then fitted to Eq. 4 using a standard least squares fitting algorithm to estimate voxel-wise $R_2^*$ values. Dynamic $\Delta R_2^*$ data was further analyzed using the established tracer kinetic model for DSC-MRI (19), expressing the relationship between the tissue response and the AIF, yielding semi-quantitative analysis of blood flow (BF) and blood volume (BV). Corresponding mean transit time (MTT) is given by the central volume principle: MTT=BV/BF. To minimize contamination due to CA recirculation and leakage, the dynamic $\Delta R_2^*$ data was fitted to a gamma-variate function. For each patient, an AIF was obtained by extracting the $\Delta R_2^*$-time curve from an artery supplying the ROI using an automatic cluster-algorithm. The voxel-wise $\Delta R_2^*$-time curves were also analyzed by estimating the maximum dynamic peak change ($R_2\text{-peak}_{enh}$) and area under the curve ($R_2^*$-AUC). Due to the early onset of the first intravascular CA passage, only data from the first multi-echo segment was used for DSC analysis.

Statistical Analysis

Statistical analysis was performed using R version 2.10.1 (R Foundation for Statistical Computing, Vienna, Austria) and MATLAB R2015a version 8.5.0 (Mathworks, Inc., Natick, Mass., USA). The following pathological stages were grouped in the statistical analysis; T1 and T2, T3 and T4, and N1 and N2. A Mann-Whitney U test was used to evaluate associations between kinetic parameters and clinicopathologic data. A p-value<0.05 was considered significant. Statistically significant parameters were further evaluated using receiver operator characteristic (ROC) curve statistics. Intraclass correlation coefficient (ICC) for continuous variables was used to evaluate interobserver agreement for the measured whole-tumor VOI.

Results

MRI Analysis

Table 2 summarizes the associations between kinetic parameters attainable with the dynamic contrast-based multi-echo sequence and histopathologic evaluation of the surgically resected specimens. For patients with histologically confirmed nodal metastasis, the primary tumor showed a significantly lower $R_2^*$-peak$_{enh}$ than patients without parameters and the pT-stage. A mismatch between mrN and pN was found in 6 of 17 patients (35.3%), corresponding to an accuracy of 64.7%.

TABLE 2

Comparison of the functional DCE- and DSC-MRI parameters with clinicopathologic data and corresponding p-values. The table shows mean parametric values based on whole-tumor medians extracted using VOI from reader 1 (A) and reader 2 (B).

A: Reader 1

| Parameters | T1 | T2 | T3 | T4 | P-values T1/T2 vs T3/T4 | N− | N+ | P-values N− vs N+ |
|---|---|---|---|---|---|---|---|---|
| *DCE-MRI analysis* | | | | | | | | |
| $K^{trans}$ | 0.142 | 0.188 | 0.182 | 0.171 | 0.673 | 0.183 | 0.171 | 0.475 |
| $k_{ep}$ | 0.562 | 0.631 | 0.559 | 0.524 | 0.606 | 0.631 | 0.524 | 0.364 |
| $v_e$ | 18.3 | 25.2 | 30.4 | 30.5 | 0.370 | 28.2 | 30.5 | 0.962 |
| $v_p$ | 6.20 | 7.33 | 5.09 | 4.67 | 0.059 | 6.82 | 4.70 | 0.161 |
| AUC | 242.4 | 360.1 | 387.7 | 362.6 | 0.321 | 370.3 | 278.9 | 0.315 |
| Peak$_{enh}$ | 1.36 | 1.90 | 1.92 | 1.70 | 0.541 | 1.90 | 1.70 | 0.417 |
| TTP | 37.1 | 34.7 | 110.8 | 122.6 | 0.046 | 44.8 | 118.0 | 0.133 |
| Wash In | 0.061 | 0.106 | 0.071 | 0.053 | 0.370 | 0.078 | 0.063 | 0.315 |
| Wash Out | 0.0050 | 0.0055 | 0.0030 | 0.0016 | 0.093 | 0.0052 | 0.0016 | 0.161 |
| *DSC-MRI analysis* | | | | | | | | |
| BF | 177.6 | 255.7 | 183.4 | 122.0 | 0.139 | 237.1 | 166.9 | 0.088 |
| BV | 22.1 | 21.1 | 15.9 | 12.4 | 0.021 | 20.6 | 14.6 | 0.109 |
| MTT | 6.60 | 4.83 | 4.54 | 4.90 | 0.200 | 4.67 | 4.90 | 0.887 |
| $R_2^*$-AUC | 445.7 | 520.4 | 431.0 | 310.8 | 0.167 | 498.2 | 339.9 | 0.070 |
| $R_2^*$-Peak$_{enh}$ | 25.5 | 39.9 | 29.9 | 15.3 | 0.321 | 35.4 | 23.4 | 0.005 |

B: Reader 2

| Parameters | T1 | T2 | T3 | T4 | P-values T1/T2 vs T3/T4 | N− | N+ | P-values N− vs N+ |
|---|---|---|---|---|---|---|---|---|
| *DCE-MRI analysis* | | | | | | | | |
| $K^{trans}$ | 0.150 | 0.192 | 0.180 | 0.169 | 1.000 | 0.187 | 0.169 | 0.364 |
| $k_{ep}$ | 0.591 | 0.541 | 0.580 | 0.469 | 0.815 | 0.562 | 0.469 | 0.601 |
| $v_e$ | 22.3 | 27.7 | 30.8 | 33.8 | 0.370 | 28.7 | 31.1 | 0.813 |
| $v_p$ | 5.0 | 7.4 | 5.2 | 4.7 | 0.423 | 6.4 | 4.7 | 0.601 |
| AUC | 230.2 | 363.6 | 380.5 | 375.7 | 0.236 | 371.7 | 278.9 | 0.475 |
| Peak$_{enh}$ | 1.32 | 1.84 | 1.91 | 1.76 | 0.481 | 1.88 | 1.71 | 0.417 |
| TTP | 40.2 | 75.7 | 113.6 | 194.3 | 0.321 | 107.2 | 118.0 | 0.475 |
| Wash In | 0.064 | 0.094 | 0.071 | 0.055 | 0.541 | 0.075 | 0.062 | 0.230 |
| Wash Out | 0.0062 | 0.0042 | 0.0018 | −0.0006 | 0.321 | 0.0047 | 0.0011 | 0.230 |
| *DSC-MRI analysis* | | | | | | | | |
| BF | 188.4 | 254.0 | 185.0 | 122.0 | 0.423 | 220.1 | 161.8 | 0.193 |
| BV | 20.7 | 18.6 | 15.8 | 12.4 | 0.167 | 18.9 | 14.1 | 0.230 |
| MTT | 7.04 | 4.63 | 4.56 | 5.08 | 0.321 | 4.70 | 5.08 | 0.887 |
| $R_2^*$-AUC | 413.9 | 512.3 | 426.4 | 298.8 | 0.321 | 502.7 | 315.0 | 0.070 |
| $R_2^*$-Peak$_{enh}$ | 23.4 | 39.8 | 29.6 | 14.6 | 0.423 | 36.0 | 23.0 | 0.019 |

Figure 1A:
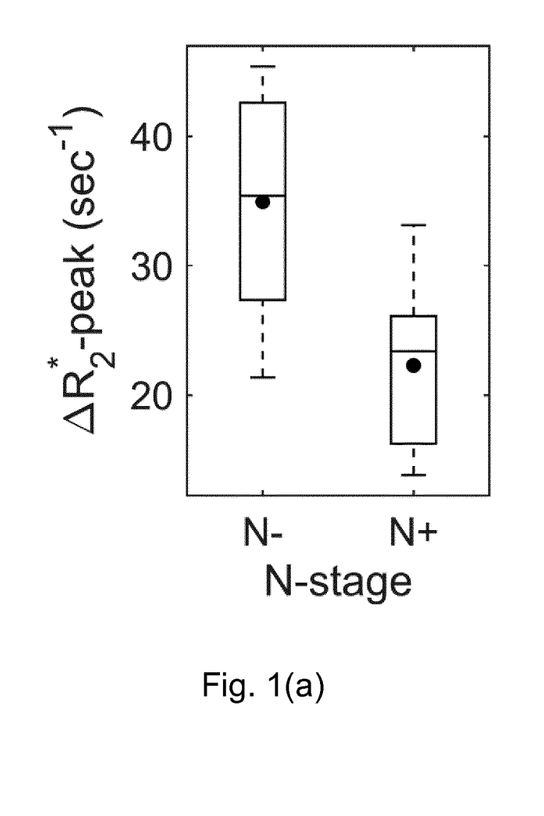
FIGS. 1(a) and 1(b) are box and whisker plots showing the parameter $R_2^*$-peak$_{enh}$ when comparing patients with and without nodal metastasis based on volumes of interest (VOI) by (a) Reader 1 and (b) Reader 2.
Figure 1B:
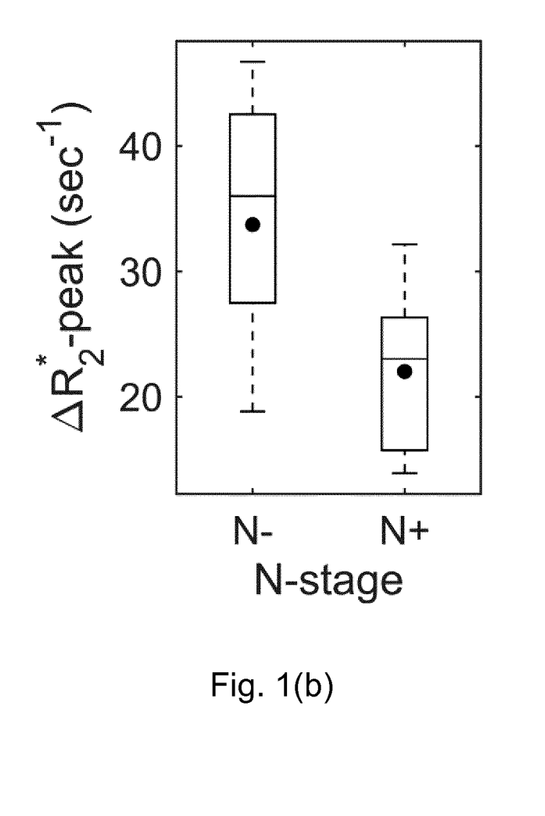

T1: n = 4; T2: n = 4; T3: n = 8; T4: n = 1; N−: n = 10; N+: n = 7. P-values at the univariate analysis were obtained by Mann-Whitney U-test. Parameters showing statistically significant differences are highlighted in bold.

nodal metastasis (See FIG. 1), corresponding to a p-value of 0.005 for Reader 1 and 0.019 for Reader 2, and an area under the ROC-curves (sensitivity, specificity) of 90 (86%, 90%) and 84 (86%, 80%), respectively. The box and whisker plots of FIGS. 1(a) and 1(b) illustrate the median (via the line inside the box) and the mean (via the circle inside box) values, interquartile range (the box itself), as well as minimal and maximal values (via the whisker lines extending above and below the box). For Reader 1, T1 and T2 cases showed a significantly shorter TTP (p=0.046) and higher BV (p=0.021), compared to T3 and T4 cases. The corresponding area under the ROC-curves (sensitivity, specificity) was 79 (71%, 90%) and 83 (71%, 90%), respectively. For Reader 2, no significant associations were found between the DCE parameters and the pT-stage.

Figure 2A:
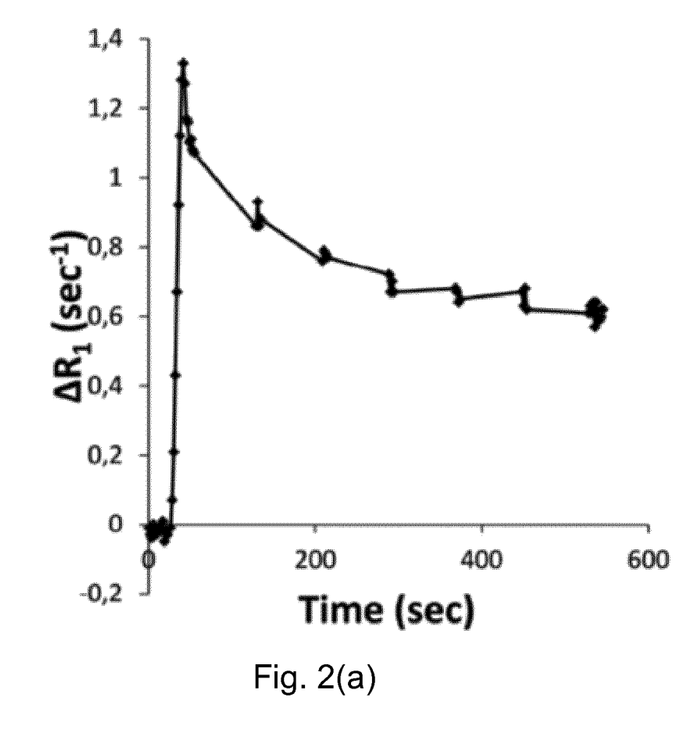
FIGS. 2(a) and 2(b) are plots of high temporal resolution $\Delta R_1$-(a) and $\Delta R_2^*$ (b) time-curves for a 66-year-old male histologically diagnosed with adenocarcinoma.
Figure 2B:
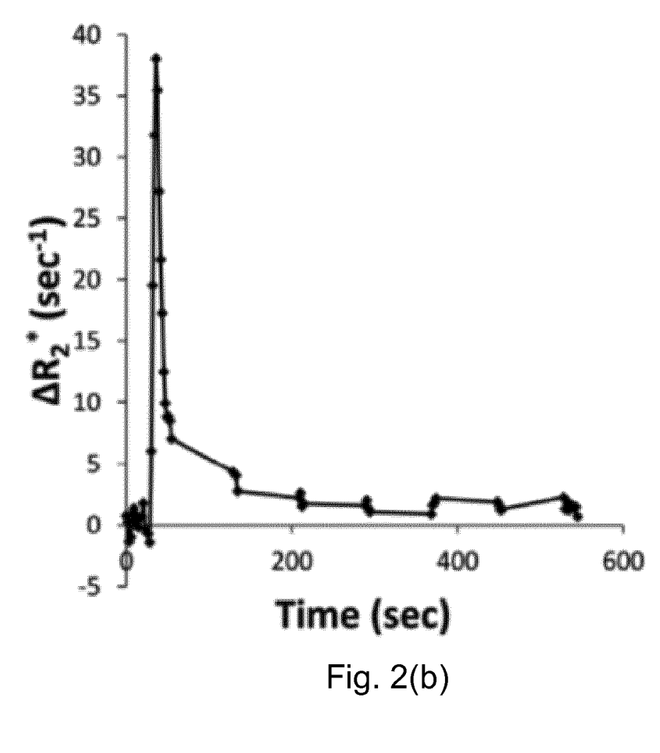

FIG. 2 shows DCE- and DSC-data obtained from the multi-echo sequence in a sample case. The curves were extracted using a circular region of interest in the center of the tumor. Resulting parametric maps (no shown) representing $K^{trans}$, $k_{ep}$, BV and $R_2^*$-peak$_{enh}$ were also obtained. The tumor showed a fast wash-in and wash-out rate in the $R_1$-data, and a strong transient increase during bolus first pass in the $R_2^*$-data.

Figure 3:
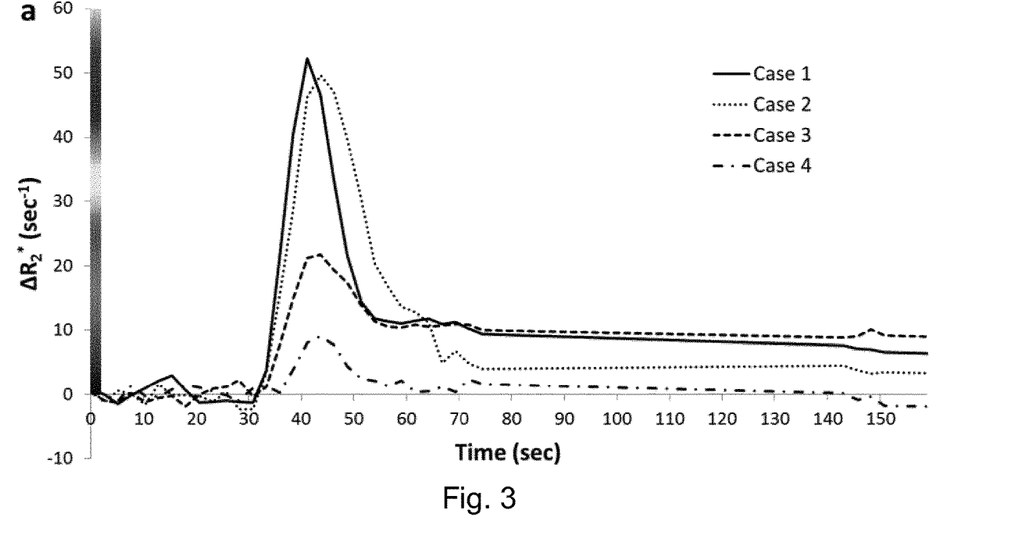
FIG. 3 is a plot of high temporal resolution $\Delta R_2^*$ time-curves from four rectal cancer patients.

FIG. 3 shows $\Delta R_2^*$ time-curves from four cases. This figure demonstrates the added value of $\Delta R_2^*$ analysis of the primary tumor in distinguishing patients with and without nodal metastasis. Corresponding $T_2$-weighted images merged with parametrical maps representing $\Delta R_2$-peak$_{enh}$ (not shown) were also obtained. The $\Delta R_2^*$ time-curves were extracted using a region of interest, drawn by an experienced radiologist and delineating the tumor at a central slice. Cases 1 and 2 showed a negative N-stage (N−), whereas cases 3 and 4 showed a positive N-stage (N+). Note the difference in $\Delta R_2^*$ time-curves where the N− tumors showed a strong transient increase during the bolus first-pass while the N+ tumors showed lower $R_2^*$-enhancement. This can also be seen in the parametric maps where the N+ tumors showed an overall low dynamic change in $R_2$ whereas the N− tumors appear highly heterogeneous with hot-spots demonstrating a strong increase in $R_2^*$.

Figure 4:
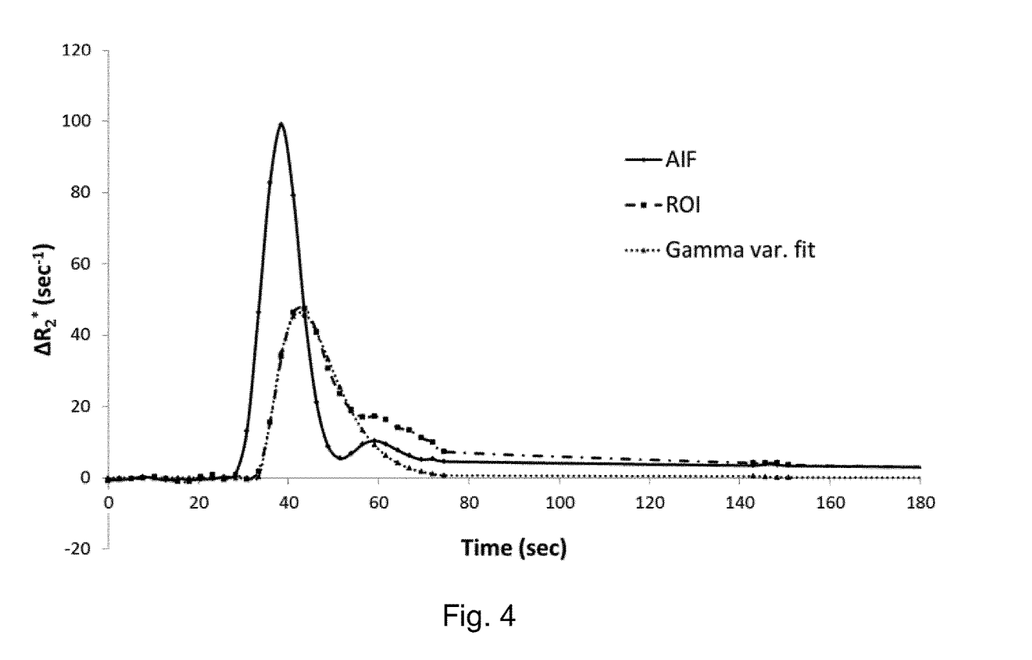
FIG. 4 shows AIF automatically detected together with the average $\Delta R_2^*$ time-curves and corresponding gamma-variate-fitted curve during bolus first pass for a 67-year-old male histologically diagnosed with adenocarcinoma.
Figure 5A:
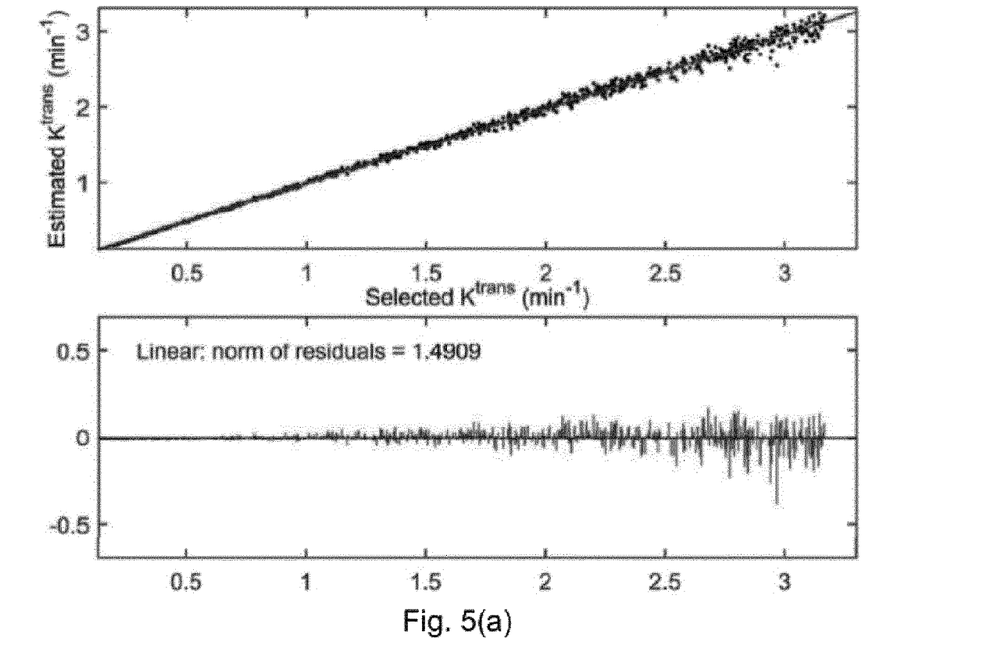
FIGS. 5(a) to 5(d) show selected $K^{trans}$ and $k_{ep}$ versus estimated $K^{trans}$ and $k_{ep}$ using a continuous dynamic acquisition (a and c) and a split dynamic acquisition (b and d), respectively, with the lower figures showing the corresponding residuals and residual norms obtained from the linear regression.
Figure 5B:
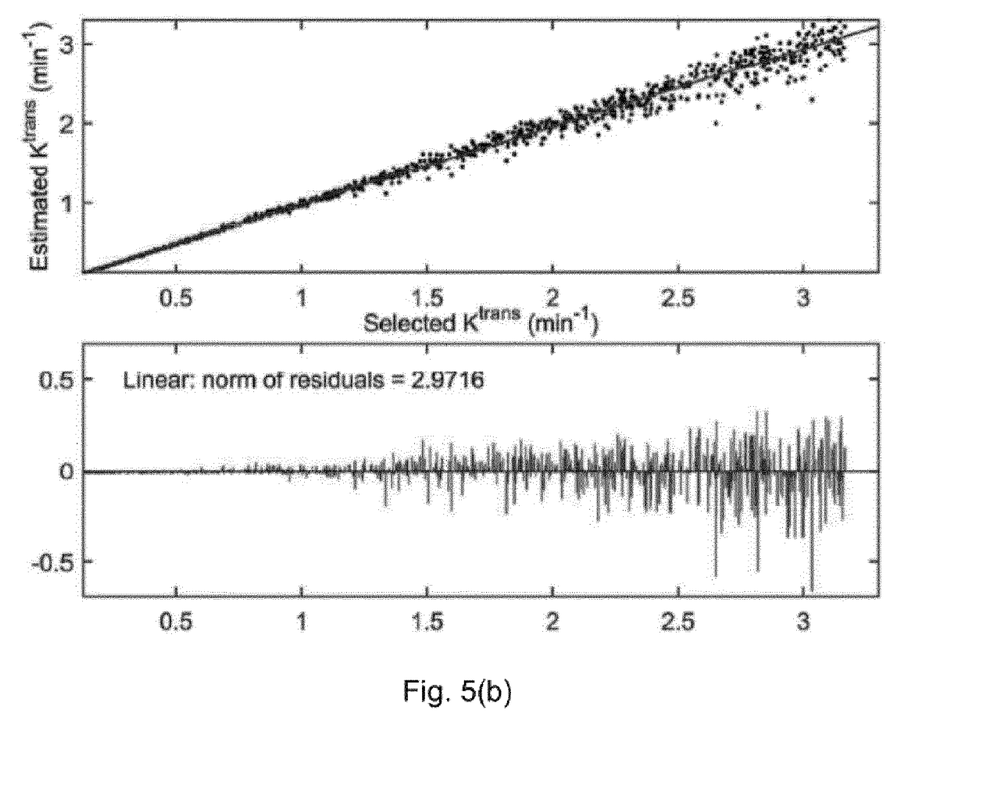
Figure 5C:
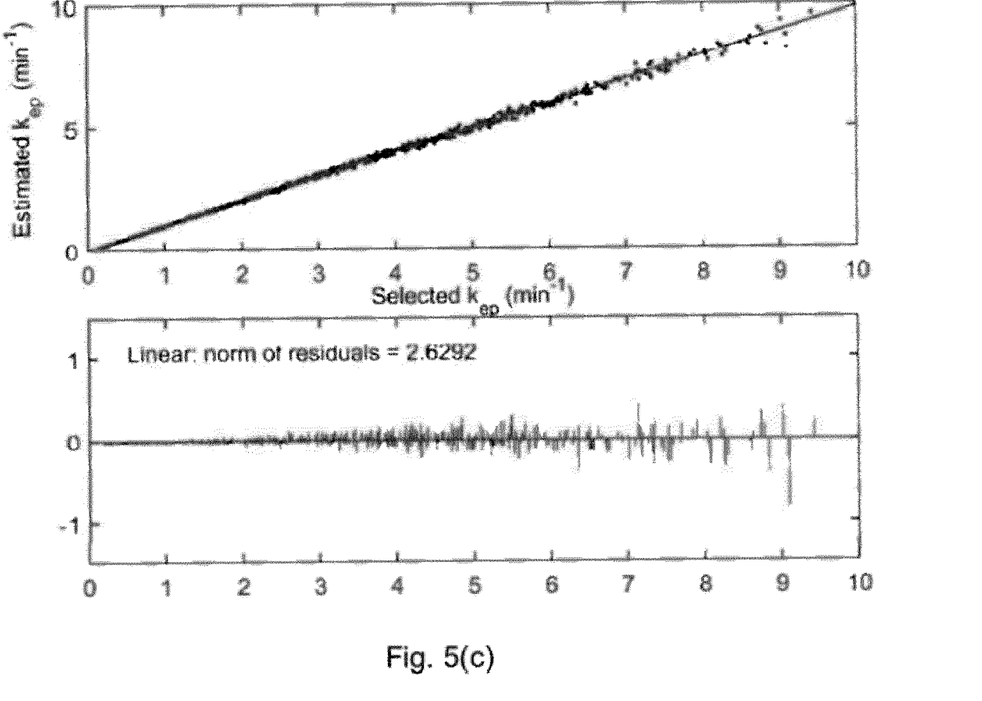
Figure 5D:
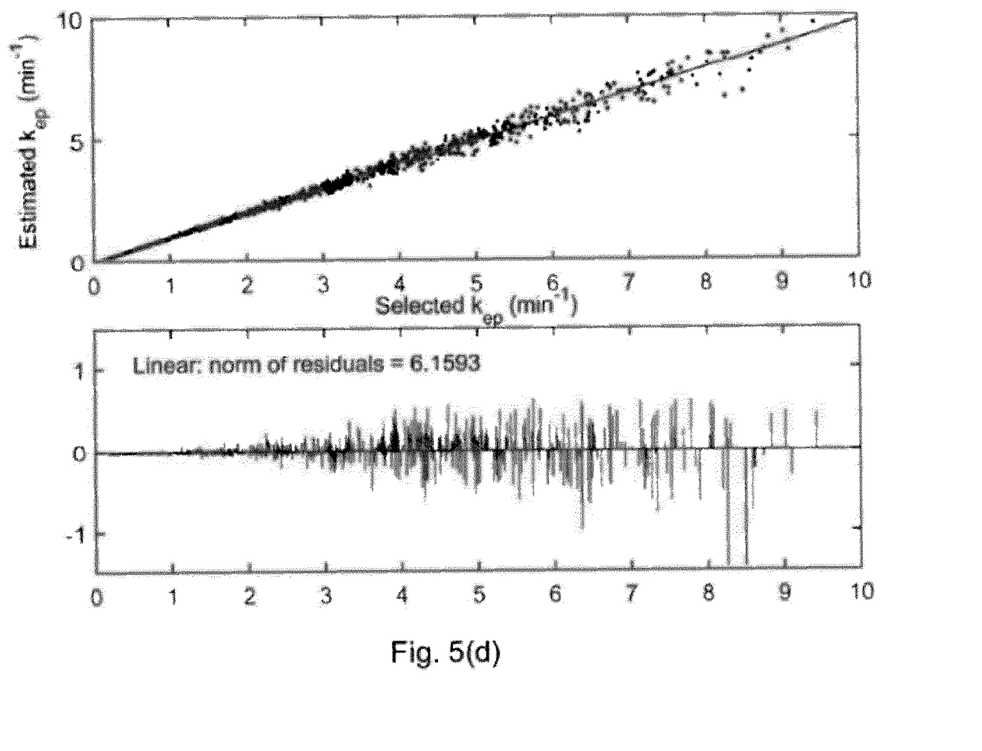

FIG. 4 shows the measured AIF- and VOI-curves together with the corresponding gamma-variate fitted curve for a selected case. The patient is a 67-year-old male histologically diagnosed with adenocarcinoma. The figure shows the AIF automatically detected together with the average $\Delta R_2^*$ time-curves during bolus first pass. The corresponding gamma-variate-fitted curve is shown as dotted line. The average $\Delta R_2^*$ time-curves were extracted from a central slice. Parametric maps representing BV and $R_2^*$-peak$_{enh}$ (not shown) were also obtained as overlay on $T_2$-weighted image. FIG. 4 demonstrates the importance of CA administration timing and acquisition length of the first multi-echo acquisition segment in order to include the first pass bolus.

The ICC (95% CI) between the two readers was 0.95 (0.87-0.98) for all whole-tumor VOIs, 0.81 (0.32-0.96) for $T_1$- and T2-stages tumor VOIs, and 0.95 (0.80-0.99) for T3- and T4-stages tumor VOIs.

FIG. 5 shows the accuracy of $K^{trans}$ and $k_{ep}$ estimations from a continuous and split dynamic acquisition for a defined range of initially selected parametric values. $K^{trans}$ and $k_{ep}$ versus estimated $K^{trans}$ and $k_{ep}$ are shown with data using a continuous dynamic acquisition (a and c) and a split dynamic acquisition (b and d), respectively. The bottom figures show the corresponding residuals and residual norms obtained from the linear regression. The residuals indicated that the dispersion of data, and thus the uncertainty of parameter estimates, increases with higher parameter values for both $K^{trans}$ and $k_{ep}$. However, the residuals were symmetrically distributed around zero in all cases suggesting absence of a systematic error in the parameter estimates. A Mann-Whitney U test showed that there was no significant difference in the estimation of neither $K^{trans}$ (p=0.71), $k_{ep}$ (p=0.81), $v_e$ (p=0.99) nor $v_p$ (p=0.71) using the two acquisition alternatives.

Figure 6:
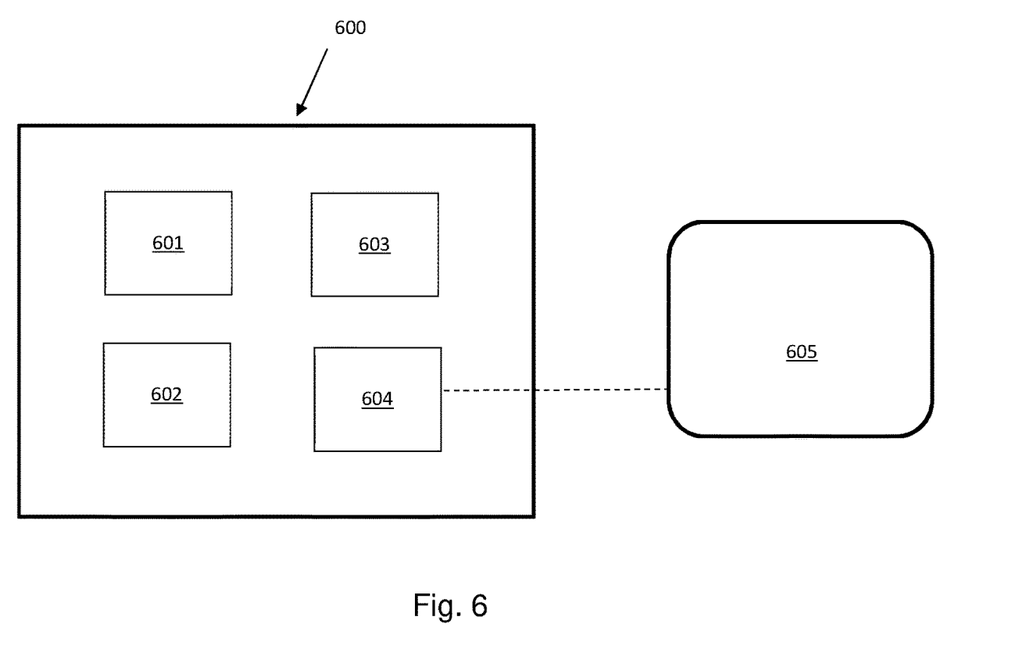
FIG. 6 is a schematic illustration of a data processing apparatus for processing MRI data for analysis of tumors.

A schematic illustration of a data processing apparatus 600 for processing MRI data for analysis of tumors is shown in FIG. 6. The data processing apparatus 600 includes an MRI data receiving module 601 for receiving dynamic contrast enhanced MRI data and dynamic susceptibility contrast MRI data for a volume of the patient's body including a tumor; a volume of interest identification module 602 for generating and/or receiving data identifying a volume of interest enclosing the tumor; an MRI data processing module 603 for processing the MRI data for the volume of interest; and an MRI control module 604 for controlling an MRI apparatus 605.

Discussion

The study described herein identified a significant association between $R_2^*$-peak$_{enh}$ in the primary rectal tumor by DSC-MRI and the nodal status evaluated by histopathology of the surgical specimen, showing an area under the ROC-curve of 90% and 84% for Reader 1 and 2, respectively. In comparison, radiological assessments of nodal status agreed with histopathological evaluation in 64.7% (11 of 17 patients). This finding is comparable to that of a recent meta-analysis (5). A lower value of $R_2^*$-peak$_{enh}$ was significantly associated with the presence of lymph node metastasis.

One hypothesis is that the peak change in $R_2^*$ reflects tissue blood supply, and that a low $R_2^*$-peak$_{enh}$ areas may be associated with hypoxic tissue caused by insufficient blood flow. The nodal status represents a main prognostic marker for metastatic progression and unfavorable survival. A positive N-stage will also have implications for treatment, as these patients should be considered for neoadjuvant therapy, and extended pelvic surgery to include all lymph nodes. DSC-MRI of rectal cancer can provide an important indicator for lymph node status, which will improve mrN staging prior to commencement of therapy.

Given that the multi-echo acquisition was run as part of a split-dynamic MRI framework, simulations were performed to investigate whether the splitting of dynamic time-series may influence the reliability of parameter estimation in comparison with a continuous acquisition. According to the simulations, the split dynamic acquisition did not significantly affect the accuracy of kinetic parameter estimates compared with using a continuous acquisition. Uncertainties in the estimates were found to increase with increasing parametric value for both acquisition methods, with a somewhat larger error in for the split dynamic approach. This may indicate that the splitting process reduces the sensitivity to accurately estimate extremely abnormal kinetic values. However, this difference was not statistically significant, and the findings suggest that essential information is not lost in the splitting process, and that a split dynamic approach will provide sufficient information of the contrast enhancement kinetics for clinically relevant parametric values.

Whereas the peak change in $R_2^*$ showed significant association with nodal status, similar association was not found in other perfusion related parameters, such as $v_p$, BV, BF and MTT. This may be because $R_2^*$-peak$_{enh}$ is a simple parameter estimate unaffected by any assumptions and sources of errors in kinetic modeling. In particular, correct identification of the AIF is challenging both for DCE- and DSC-MRI in this region, and kinetic parameters derived from AIF deconvolution may therefore be more inaccurate than metrics derived from the raw tissue response. Also, due to a relatively long TE, the first echo used for DCE analysis may be affected by $T_2^*$ signal attenuation, especially for high CA concentrations in blood, which may result in an additional errors in the DCE-derived parameters such as $K^{trans}$ and $v_p$. However, given the multi-echo acquisition, $T_2^*$ signal attenuation in DCE-data may be corrected for by including $\Delta R_2^*$-data when estimating the change in $R_1$.

In conclusion, a dynamic contrast-based multi-echo MRI technique has been implemented and tested in rectal cancer patients. This showed a significant association between the peak change in tumor $R_2^*$ during bolus first pass and nodal status, suggesting that DSC-MRI may help to determine N-status in diagnostic rectal cancer staging.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A method for processing MRI data for analysis of rectal tumors, the method comprising:
   obtaining dynamic contrast enhanced MRI data and dynamic susceptibility contrast MRI data for a volume of the patient's body including a rectal tumor;
   identifying a volume of interest enclosing the rectal tumor;
   processing the MRI data for the volume of interest in order to identify one or more parameters relating to the transverse relaxation rate and/or to dynamic changes in the transverse relaxation rate, wherein the one or more parameters relating to the transverse relaxation rate and/or to dynamic changes in the transverse relaxation rate include one or more of: the peak change in tumor $R_2^*$, the dynamic peak change in tumor $R_2^*$, a maximum of the peak change or the dynamic peak change, and/or an integral for dynamic peak change in tumor $R_2^*$ over a time period;
   comparing the one or more parameters to previously obtained similar parameters for multiple other patients having similar rectal tumors that are either known to exhibit lymph node metastasis or are known not to exhibit lymph node metastasis; and
   thereby determining if the MRI data indicates that the rectal tumor is at a greater risk of exhibiting lymph node metastasis or at a lesser risk of exhibiting lymph node metastasis.

2. The method as claimed in claim 1, comprising determining if the MRI data indicates a patient with a rectal tumor at greater risk of exhibiting lymph node metastasis by comparison of the one or more parameters with the previously obtained similar parameters and determining if the one or more parameters are similar to previously obtained similar parameters for patients having similar rectal tumors that are known to exhibit lymph node metastasis.

3. The method as claimed in claim 1, comprising determining if the MRI data indicates a patient with a rectal tumor at greater risk of exhibiting lymph node metastasis by comparison of the one or more parameters with the previously obtained similar parameters and determining if the one or more parameters are lower than previously obtained similar parameters for patients having similar rectal tumors that are known not to exhibit lymph node metastasis.

4. The method as claimed in claim 1, wherein the comparison includes the use of a threshold value determined based on the previously obtained similar parameters.

5. The method as claimed in claim 4, wherein the threshold value is a value lying between the previously obtained similar parameters for patients having similar rectal tumors that are known to exhibit lymph node metastasis and the previously obtained similar parameters for patients having similar rectal tumors that are known not to exhibit lymph node metastasis.

6. The method as claimed in claim 1, wherein the tumor $R_2^*$ is wash-in $R_2^*$ peak enhancement.

7. The method as claimed in claim 1, wherein both of the dynamic contrast enhanced MRI data and the dynamic susceptibility contrast MRI data are obtained in a single dynamic examination.

8. A system comprising dynamic contrast enhanced MRI data and dynamic susceptibility contrast MRI data for a volume of the patient's body including a rectal tumor along with data processing apparatus for processing the MRI data for analysis of rectal tumors, wherein the data processing apparatus comprises:
   an MRI data receiving module for receiving the dynamic contrast enhanced MRI data and dynamic susceptibility contrast MRI data;
   a volume of interest identification module for generating and/or receiving data identifying a volume of interest enclosing the rectal tumor;
   data storage; and
   an MRI data processing module for processing the MRI data for the volume of interest and being arranged to:
      identify one or more parameters relating to the transverse relaxation rate and/or to dynamic changes in the transverse relaxation rate, wherein the one or more parameters relating to the transverse relaxation rate and/or to dynamic changes in the transverse relaxation rate include one or more of: the peak change in tumor $R_2^*$, the dynamic peak change in tumor $R_2^*$, a maximum of the peak change or the dynamic peak change, and/or an integral for dynamic peak change in tumor $R_2^*$ over a time period,
      compare the one or more parameters to previously obtained similar parameters for multiple other patients having similar rectal tumors that are either known to exhibit lymph node metastasis or are known not to exhibit lymph node metastasis, wherein the previously obtained similar parameters for rectal tumors are stored on the data storage and accessed therefrom by the MRI data processing module, and
      thereby determine if the MRI data indicates that the rectal tumor is at a greater risk of exhibiting lymph node metastasis or at a lesser risk of exhibiting lymph node metastasis.

9. The data processing apparatus as claimed in claim 8, wherein the data processing module is arranged to determine if the MRI data indicates a patient with a rectal tumor at greater risk of exhibiting lymph node metastasis by comparison of the one or more parameters with the previously obtained similar parameters and determining if the one or more parameters are similar to previously obtained similar parameters for patients having similar rectal tumors that are known to exhibit lymph node metastasis.

10. The data processing apparatus as claimed in claim 8, wherein the data processing module is arranged to determine if the MRI data indicates a patient with a rectal tumor at greater risk of exhibiting lymph node metastasis by comparison of the one or more parameters with the previously obtained similar parameters and determining if the one or more parameters are lower than previously obtained similar parameters for patients having similar rectal tumors that are known not to exhibit lymph node metastasis.

11. The data processing apparatus as claimed in claim 8, wherein the data processing apparatus is arranged to compare the one or more parameters to previously obtained similar parameters using a threshold value determined based on the previously obtained similar parameters, wherein the threshold value is a value lying between the previously obtained similar parameters for patients having similar rectal tumors that are known to exhibit lymph node metastasis and the previously obtained similar parameters for patients having similar rectal tumors that are known not to exhibit lymph node metastasis.

12. The data processing apparatus as claimed in claim 8, wherein the tumor $R_2^*$ is wash-in $R_2^*$ peak enhancement.

13. The data processing apparatus as claimed in claim 8, comprising an MRI control module for controlling an MRI apparatus in order to obtain both of the dynamic contrast enhanced MRI data and the dynamic susceptibility contrast MRI in a single dynamic examination.

14. A non-transitory computer readable medium comprising a computer program product containing instruction that, when executed, will configure a data processing apparatus to:

receive dynamic contrast enhanced MRI data and dynamic susceptibility contrast MRI data for a volume of the patient's body including a rectal tumor;

receive data identifying a volume of interest enclosing the rectal tumor;

process the MRI data for the volume of interest in order to identify one or more parameters relating to the transverse relaxation rate and/or to dynamic changes in the transverse relaxation rate, wherein the one or more parameters relating to the transverse relaxation rate and/or to dynamic changes in the transverse relaxation rate include one or more of: the peak change in tumor $R_2^*$, the dynamic peak change in tumor $R_2^*$, a maximum of the peak change or the dynamic peak change, and/or an integral for dynamic peak change in tumor $R_2^*$ over a time period;

compare the one or more parameters to previously obtained similar parameters for multiple other patients having similar rectal tumors that are either known to exhibit lymph node metastasis or are known not to exhibit lymph node metastasis; and thereby determine if the MRI data indicates that the rectal tumor is at a greater risk of exhibiting lymph node metastasis or at a lesser risk of exhibiting lymph node metastasis.

\* \* \* \* \*